United States Patent
Spasovski et al.

(10) Patent No.: US 11,284,793 B2
(45) Date of Patent: Mar. 29, 2022

(54) METHOD AND DEVICE FOR DETERMINING THE ORIENTATION OF THE EYE DURING EYE SURGERIES

(71) Applicant: CHRONOS VISION GMBH, Berlin (DE)

(72) Inventors: Saso Spasovski, Berlin (DE); Kai Just, Bonn (DE); Wolfgang Pogade, Berlin (DE)

(73) Assignee: CHRONOS VISION GMBH, Berlin (DE)

( * ) Notice: Subject to any disclaimer, the term of this patent is extended or adjusted under 35 U.S.C. 154(b) by 1224 days.

(21) Appl. No.: 15/312,289

(22) PCT Filed: May 13, 2015

(86) PCT No.: PCT/DE2015/000242
§ 371 (c)(1),
(2) Date: Nov. 18, 2016

(87) PCT Pub. No.: WO2015/176699
PCT Pub. Date: Nov. 26, 2015

(65) Prior Publication Data
US 2017/0215726 A1     Aug. 3, 2017

(30) Foreign Application Priority Data

May 19, 2014   (DE) .................. 10 2014 106 993.5

(51) Int. Cl.
*A61B 3/113*     (2006.01)
*A61F 9/008*     (2006.01)
(Continued)

(52) U.S. Cl.
CPC ............ *A61B 3/113* (2013.01); *A61B 3/0008* (2013.01); *A61B 34/20* (2016.02);
(Continued)

(58) Field of Classification Search
CPC ....... A61B 3/113; A61B 3/0008; A61B 34/20; A61B 2034/2065; A61B 2034/2055;
(Continued)

(56) References Cited

U.S. PATENT DOCUMENTS 4,538,608 A * 9/1985 L'Esperance, Jr. ......................... A61F 9/00736
372/24
8,414,123 B2 4/2013 Boukhny et al.
(Continued)

FOREIGN PATENT DOCUMENTS

DE    102008034490 A1    2/2010
DE    102009053208 A1    8/2011
(Continued)

OTHER PUBLICATIONS

International Search Report dated Feb. 5, 2016 in International Application No. PCT/DE2015/000242.

*Primary Examiner* — Gary Jackson
*Assistant Examiner* — Sebastian X Lukjan
(74) *Attorney, Agent, or Firm* — Hauptman Ham, LLP (57) ABSTRACT

Disclosed are a method and a device for controlling an eye surgery system, wherein a light pattern is generated on an eye by an illumination device and is captured by a camera unit while the patient is in the position in which he or she will undergo the surgery. At least one property of the eye characterizing the current orientation of the eye during the surgery is determined from the light pattern by a computing unit.

24 Claims, 9 Drawing Sheets

(51) Int. Cl.
   *A61B 34/20*   (2016.01)
   *A61B 3/00*   (2006.01)

(52) U.S. Cl.
   CPC ...... *A61F 9/00802* (2013.01); *A61F 9/00812* (2013.01); *A61F 9/00825* (2013.01); *A61B 2034/2055* (2016.02); *A61B 2034/2065* (2016.02); *A61F 2009/00846* (2013.01)

(58) Field of Classification Search
   CPC .............. A61F 9/00825; A61F 9/00802; A61F 9/00812; A61F 2009/00846
   See application file for complete search history.

(56) References Cited

U.S. PATENT DOCUMENTS

| | | | |
|---|---|---|---|
| 2005/0197655 A1* | 9/2005 | Telfair | A61B 18/20 606/5 |
| 2008/0074615 A1* | 3/2008 | Lai | A61B 3/0083 351/206 |
| 2009/0275929 A1* | 11/2009 | Zickler | A61B 3/113 606/5 |
| 2011/0122365 A1 | 5/2011 | Kraus et al. | |
| 2011/0230751 A1 | 9/2011 | Kersting | |
| 2012/0197102 A1 | 8/2012 | Hanebuchi et al. | |
| 2012/0265181 A1* | 10/2012 | Frey | A61B 3/1035 606/5 |
| 2013/0296834 A1 | 11/2013 | Wellhoefer et al. | |
| 2015/0018674 A1* | 1/2015 | Scott | A61F 9/00827 600/427 |
| 2016/0089271 A1* | 3/2016 | Zacharias | A61F 9/00825 606/5 |
| 2016/0262617 A1* | 9/2016 | Gerrans | B33Y 50/00 |

FOREIGN PATENT DOCUMENTS

| | | | |
|---|---|---|---|
| DE | 102010013986 A1 | 10/2011 | |
| DE | 102012008998 A1 | 11/2013 | |
| EP | 2184005 B1 | 5/2011 | |
| KR | 20140008457 A | 1/2014 | |
| WO | 99/23936 A2 | 5/1999 | |
| WO | WO-9923936 A2 * | 5/1999 | ............ A61B 3/113 |
| WO | 2009135084 A1 | 11/2009 | |
| WO | 2010009897 A1 | 1/2010 | |
| WO | 2010046371 A1 | 4/2010 | |
| WO | 2012041349 A1 | 4/2012 | |

* cited by examiner

METHOD AND DEVICE FOR DETERMINING THE ORIENTATION OF THE EYE DURING EYE SURGERIES

RELATED APPLICATIONS

The present application is a National Phase of International Application Number PCT/DE2015/000242, filed May 13, 2015, and claims priority from German Application Number 10 2014 106 993.5, filed May 19, 2014.

The invention relates to a method and an apparatus for determining the orientation of the eye during eye operations, and to an operating microscope, a control unit and a computer program for eye surgery systems.

Often, the last resort for patients suffering a common age-related opacity of the natural eye lens—called a cataract—only lies in removing the lens situated within the eye and implanting an artificial intraocular lens, abbreviated to IOL.

Whereas only spherically shaped IOLs were used in the past, medical advancement in the meantime also allows the use of aspherically formed lenses, the main purpose of which lies in compensating the imaging aberrations of an irregularly curved cornea. Astigmatism is a particularly frequently occurring type of corneal irregularity. In this refractive error, the light entering the eye is not refracted uniformly and focused at a point. In the case of astigmatism, the cornea does not have constant curvature but can, to a good approximation, be approximated by a torus surface which may be characterized by two values of curvature along two mutually perpendicular surface directions. In one direction, the cornea has the smallest curvature (flat corneal axis), whereas the corneal curvature perpendicular thereto is at a maximum (steep corneal axis). For complete characterization of the astigmatism, there also needs to be, in addition to the two aforementioned values of curvature, a specification about the orientation of the direction with e.g. the greatest curvature, the so-called axis position.

Diverse diagnostic machines are used for determining the surface curvature and e.g. the astigmatism axis of the eye. With a few exceptions, these are based on the evaluation of eye images in which the distances between the either punctiform or ring-like reflections, which arise on the corneal surface as a result of an appropriate illumination arrangement, are analyzed. Thus, the reflections of an e.g. planar, circular arrangement of light-emitting diodes appear arranged like an ellipse in the camera image in the case of an astigmatic eye.

An intraocular lens seeking to compensate this defective formation of the cornea must itself be formed in a geometrically similar manner. To this end, use is made of toric lenses which are distinguished by virtue of, in particular, having a maximum curvature and a minimum curvature in two mutually perpendicular directions. The axis of a toric intraocular lens is characterized by markings applied to the lens surface. Usually, these markings consist of points or lines, the imaginary connecting line of which defines the lens axis.

For the purposes of an ideal correction of the corneal astigmatism, the toric intraocular lens must be aligned exactly during insertion into the eye, i.e. it must be rotated by the medical practitioner during the operation in such a way that the axis thereof corresponds to the best possible extent to the astigmatism axis of the cornea which was determined during the diagnosis at an earlier time. However, the problem here is that the relative torsional orientation of the eye between the diagnostic measurement and the time of the operation may generally not be assumed to be constant and known.

Document WO 2010/009897 A1 describes an eye surgery system and corresponding method, in which a presurgical first image of an eye to be operated on is stored in an image memory. A camera serves for recording a second image of the eye to be operated on intraoperatively. An image processing apparatus establishes an orientation value from the first image and the second image. A display apparatus generates a display of a marking depending on the orientation value.

Document WO 2010/046371 A1 describes an image processing method for computer-assisted eye operations. Here, a reference image of the eye is recorded and enhanced with context information. The reference image is registered with a real-time image of the eye and the context information is overlaid onto the real-time image in such a way that it is reproduced at the same position, independently of an eye movement.

DE 10 2009 053 208 A1 describes an apparatus for eye operations comprising an image recognition apparatus which monitors the operation process and analyzes it qualitatively in order to provide the surgeon with feedback. The subject matter of the feedback may be the guidance of an operating instrument or the lateral or rotative displacement or rotation of an intraocular lens.

Further documents in this field include, for example, U.S. Pat. No. 8,414,123 B2, EP 2184005 B1, WO 2012041349 A1 and DE102008034490 A1.

In the prior art, a registration is carried out as an integral component, i.e. a presurgical image is compared to a surgical image in order to determine the torsion therefrom.

However, the correct orientation plays a decisive role not only in the case of toric lenses and astigmatic eyes. Rather, it is always important whenever the intraocular lens does not have cylindrical symmetry in respect of the geometry or other properties, e.g. optical properties. Thus, aspherical intraocular lenses which do not have a toric form and, for example, attempt to compensate a patient-specific keratoconus are also conceivable, as are multifocal lenses with a likewise patient-specific and not necessarily cylinder-symmetrical arrangement of the various zones. These geometries also require an orientation of the lenses with a correct torsional position.

Similar problems also occur in other types of refractive operations. Examples specified here are laser treatments of the eye such as e.g. so-called LASIK operations or PRK operations. In these operations, corneal tissue is ablated in a defined manner by means of laser bombardment in order to correct refractive errors of the eye. The ablation patterns are based on a presurgical diagnosis and need not necessarily be cylindrically symmetric. By way of example, in the case of astigmatic eyes, the ablation pattern is only symmetrical in relation to the astigmatism axis. Hence, knowledge about the eye torsion between diagnosis and the current orientation during the operation is also much needed here for a rotation of the shot coordinate lists of the laser.

The relative rotation of the eye about the viewing axis between the time of diagnosis and immediately prior to the surgical intervention is often referred to as static torsion. If no further measures are taken up, this always occurs with a high probability. A plurality of factors may be responsible for this.

On the one hand, the cameras used during the diagnosis and the operation may have been rotated with respect to one another relative to the head of the patient or the position of the head relative to the camera may have changed during the operation in relation to the posture during the diagnosis. On the other hand, there may in fact be an actual torsional eye movement during the transition from a seated position during the diagnosis to a lying position of the patient during the operation.

In addition to static torsion, so-called dynamic torsion may additionally occur intraoperatively. The cause of this lies in acute torsional eye movements, in the further head movements of the patient or else it is possibly induced by the medical practitioner as a result of using operating instruments.

Currently, use is mainly made of three automated or semi-automated methods for avoiding torsion-caused orientation errors when inserting an intraocular lens. In one method, which is used very often, the patient eye is marked with a stamp and water-insoluble ink. The orientation of the astigmatism axis of the eye ascertained during the diagnosis is then specified relative to this marking. During the operation, these markers may be detected by means of e.g. image processing algorithms.

So-called surgery guidance systems identify the position of the markings and superimpose e.g. the intended position of the lens axis relative to the detected markings into the beam path of the microscope, and hence in a manner visible to the medical practitioner.

In theory, newer known methods do not require any markings. By way of example, visible anatomical properties of the eye may be used to ascertain the eye torsion between diagnosis and operation. The blood vessels of the sclera or conjunctiva, or the iris pattern lend themselves to this.

A disadvantage in these methods lies in the fact that it is very often the case that no iris patterns are visible during the operation since the pupil is usually dilated by medication and, secondly, too few blood vessels, or only non-prominent blood vessels, may be present or may be covered by the eyelids during the diagnosis.

Also, scleral hematomas, which superpose the scleral vessels in such a way that a registration of the diagnostic image with an eye image from the operation after removal of the natural lens is made more difficult or even impossible, often occur during the lensectomy (lens removal), specifically during the lens fragmentation by means of femtosecond lasers, as a result of a mechanical suction and fixation process of the eye.

Other known methods and systems are based on the evaluation of light wavefronts which, overall, permit a statement to be made about the optical properties of the eye. Once the natural lens has been removed, the cornea remains as only refracting surface. A measurement at this time establishes the refractive errors of the cornea alone and e.g. permits a statement to be made about the orientation of the astigmatism axis. A particular disadvantage of such systems is the dependence of the results on all factors influencing the refraction of light, such as e.g. mechanical deformations of the cornea by operating instruments, gas bubbles in e.g. the anterior chamber of the eye or the use of viscoelastics.

In addition to the above-described automated or semi-automated methods for avoiding IOL orientation errors, there still are a number of further semi-automated or manual methods which will not be discussed in any more detail. Here, the torsion is also determined by the medical practitioner in one way or another, for example by manually overlaying polar-transformed images which each represent the ring-like image region beyond the limbus during the diagnosis and during the operation.

Currently, the intended orientation of the lens axis of the intraocular lens to be inserted is optically superimposed into the beam path of the operating microscope during cataract operations and it appears to the medical practitioner as if embedded into the image scene. Alternatively, there is the option of displaying the operation scene observed by a camera, including the intended position of the IOL axis, online on an external monitor. With the aid of these displays, the medical practitioner may rotate the inserted intraocular lens until the markings on the lens coincide with the superimposed intended axis. In addition to the aforementioned torsion, non-torsional head or eye movements also occur naturally; these may be detected by tracking algorithms. Using this, it is possible to realize a display of the intended axis, which migrates with the eye, and further relevant information.

In types of operations in which the natural lens remains in the eye and the correction of the visual defect is intended to be obtained by reshaping the cornea by means of laser ablation, the torsion is determined indirectly in a similar manner, i.e. image processing ascertains the relative twist of a current operation image in relation to a reference image from the diagnosis. This may be a multi-stage process within the meaning of the image processing initially calculating the torsion between a diagnostic image and an operation image, the operation image still showing the eye prior to the actual intervention and this operation image subsequently being set as a new reference to which all subsequent operation images are related when calculating the dynamic torsion.

In contrast to cataract operations in which the pupil is dilated by medicaments, it is usually also possible to resort to the iris pattern for ascertaining the torsion in the case of refractive corneal operations. However, the problem arising here is that machines which produce a multiplicity of e.g. bright rings on the eye surface for ascertaining the topography of the cornea may be used during the diagnosis and therefore may cover iris structures, the latter thereby becoming useless for the algorithms. This has a disadvantage for the calculation of the torsion or, in certain circumstances, also renders it too inaccurate or impossible.

The problem arising with the intent of using blood vessels as features for registration is that, although these are usually easily visible during the diagnosis, they generally cannot be perceived by the camera during the operation since IR light is used for illumination purposes. Hence, it is currently only the iris which remains as a feature carrier when calculating the torsion.

An additional difficulty arising when calculating the torsion, in particular intraoperatively, is that the iris and the features contained therein become ever more unclear as the treatment progresses. This is due to the corneal surface becoming ever rougher during the laser ablation. As a result, the transparency reduces and the iris features may, under certain circumstances, no longer be used for calculating the torsion. A similar effect arises in the case of the so-called flap incision in LASIK operations. The cut surface generally has roughness which has a disadvantageous effect on the detection of the iris patterns, independently of whether the incision was performed with a microkeratome or by means of the femtosecond laser (femto-LASIK).

It is an object of the invention to overcome the aforementioned disadvantages of the known systems and methods, and increase the accuracy of surgical interventions in the eye. In particular, the accuracy should be increased when inserting intraocular lenses and when performing laser ablations, and the resulting vision after the intervention should be improved.

This object is achieved by the method in accordance with patent claim 1, by the apparatus in accordance with patent claim 12, by the operating microscope in accordance with patent claim 20, by the control unit for eye surgery systems in accordance with patent claim and by the computer program in accordance with patent claim 22. Further advantageous features emerge from the dependent claims, the description and the drawings.

Advantages and properties which are specified in conjunction with the features of the method according to the invention also apply, mutatis mutandis, to the features of the apparatus according to the invention, and vice versa.

The method according to the invention for determining the orientation of the eye during eye operations comprises the following steps: generating a light pattern on the eye and capturing the light pattern while the patient is in the operation position; and determining at least one property of the eye from the light pattern captured when the patient is in the operation position, said property characterizing the current orientation of the eye.

As a result of the relevant properties or parameters of the eye being determined directly during the operation, these are independent from the image material of the diagnosis. In particular, the torsion of the eye which took place between the time of diagnosis and the time of the intervention is no longer damaging to the operation result since the torsion is determined intraoperatively, i.e. when he is already in the operation position, which also includes the period of time during the operation. The torsional position of the eye at the time of diagnosis no longer plays any role. Instead, only the current orientation of the eye during the operation is of importance.

As a result of this approach, the problems and obstacles existing in the prior art are overcome as there is neither a dependence on the existence of blood vessels and iris structures which are simultaneously visible in the diagnostic image and operation image and nor do the scleral hematomas induced by fixing the eye during the lens fragmentation by means of the femtosecond laser during the lensectomy constitute a problem in the registration between diagnostic image and operation image. In particular, it is possible, e.g. in the case of cataract operations, to dispense with ascertaining the torsional difference to the time of diagnosis.

By way of example, the ascertained property of the eye may be a one-dimensional or multi-dimensional parameter. By way of example, the property or the parameter has a geometric, differential geometric, topographic or optical nature.

Preferably, the property determined from the light pattern is used to control a light marking on the eye depending on the current orientation of the eye. As a result, the medical practitioner obtains important assistance for the operation. However, it may also be used during a laser treatment for correcting the position of the ablation locations depending on the current orientation of the eye. As a result, the accuracy of laser treatments is increased.

Advantageously, the property ascertained from the light pattern is a specific topographic property of the eye. By way of example, it may characterize the iris surface, the scleral surface or else the corneal surface.

In particular, the property or the parameter ascertained from the light pattern characterizes the position of the astigmatism axis of the eye and/or a direction with a defined relationship thereto. As a result, it is possible, for example, to insert intraocular lenses exactly in the right position without a torsion of the eye, which took place between the time of diagnosis and the time of the insertion of the intraocular lens, playing any role.

The property ascertained from the light pattern is preferably determined by collecting data of the eye during the operation, the data, in particular, being obtained from topometric, topographic, keratometric, keratographic or ophthalmometric measurements.

Preferably, the current data, or variables derivable therefrom, are compared to corresponding data ascertained during the diagnosis, or variables derivable therefrom, in order to determine a change in position during the operation in relation to the time of diagnosis. In particular, a current torsion of the eye may be determined as change in position.

As a result, in particular, it is possible to ascertain a torsional relationship to equivalent parameters of the eye at the time of diagnosis. That is to say, it is possible to determine the current torsion in relation to the torsion at the time of diagnosis by comparing the position of the current eye data and parameters or properties derivable therefrom to corresponding data or parameters derivable therefrom from the diagnosis which, for example, characterize the astigmatism axis. Using this, a refractive laser treatment may also be controlled more exactly where necessary.

By way of example, the data collected during the operation and the associated images are stored and used as reference data or reference images for the subsequent steps for calculating the intraoperative change in position, in particular the torsion.

By way of example, there is a repeated or renewed ascertainment of the relevant parameters of the eye.

Advantageously, one or more eye images from the operation, for which the aforementioned data were collected and which e.g. characterize the astigmatism axis, are stored and used as reference images for the subsequent step. Then, in the subsequent step, the intraoperative torsion is determined between a current operation image, which shows the eye at a time after storing one of these reference images, and one of these reference images using means of image processing.

As a result, it is possible to update the shot positions of the laser accordingly in the case of torsions of the eye during the operation, for example in the case of refractive operations such as e.g. LASIK or PRK.

In particular, the treatment during a refractive laser operation is adapted or corrected on the basis of the current ascertained property of the eye in accordance with the invention. By way of example, this can be carried out by aligning the shot pattern of the ablation laser on the basis of the currently ascertained geometric parameters of the eye during the laser treatment.

The light marking generated on the eye on the basis of the geometric or topographic property advantageously indicates the current orientation of the eye on the eye during the eye operation, in particular in relation to the angle of rotation about the axis of the viewing direction, and/or a location marking required for the operation. By way of example, on the eye, the light marking indicates the intended alignment of an intraocular lens to be inserted into the eye and/or the intended position of a cut or incision to be carried out during the eye operation.

In particular, the light marking indicates the direction of the astigmatism axis of the eye on the eye during the eye operation. Optionally, it is also possible to indicate an axis with a defined relationship to the astigmatism axis. As a result, the medical practitioner may, for example, exactly orient an intraocular lens during the insertion on the basis of the astigmatism axis or axes with a relationship thereto.

As a result of these features, the medical practitioner is provided with information which, for example, allow him to correctly orient a lens which is not cylindrically symmetric in terms of shape and property or else exactly place an incision. As a result, he is provided with important assistance or aid. Specifying the astigmatism axis of the eye or an axis with a defined relationship thereto may, for example, take place in the current operation image when inserting a toric intraocular lens.

Advantageously, the light pattern on the eye is generated by a diffuse or afocal illumination source. In particular, a diffuse or afocal illumination offers two substantial advantages. On the one hand, it is possible to realize very specific reflection forms in a simple manner and, on the other hand, the necessity of an exact alignment, as is required in the case of focused illumination, is dispensed with. The alignment of the illumination to the distance of the eye from the microscope and to the distance of the illumination device from the eye need not be adapted to generate reflections which are detectable by the camera. By way of example, scattering films or glass panes as an attachment for e.g. LEDs or optical waveguides may be used to generate an afocal illumination.

The diffuse or afocal light sources should generate reflections which may be observed by the camera. By way of example, the astigmatism axis may be deduced from the position of the reflections. The diffuse character of these light sources facilitates shaping and is extremely tolerant in relation to a varying distance from the eye and in relation to the distance between the eye and camera.

Afocal means that the emitted light does not have a preferential direction as would be the case, for example, when using an LED. In general, the latter focuses the light by the shape of the housing thereof. If this focusing is too pronounced, it may be the case that the reflections are either no longer perceived by the camera or else no longer appear uniformly bright to the camera in certain conditions (inexpedient emission direction at specific distances of the LED from the eye and of the eye from the camera). However, said uniform brightness is important for the image processing which, for example, must ascertain the position of the reflections in the image by way of threshold operations.

A further advantage of diffuse light sources is the capability of specifically shaping reflections. Using a focused, i.e. focal, illumination, it is not possible to generate a specifically shaped light source (circle, rhombus, triangle, etc.), the specific shape of which may also be perceived as such by a camera after reflection at the highly reflective cornea.

In particular, the light pattern generated on the eye comprises specific reflection shapes. The advantage of specific reflection shapes lies, in particular, in the fact that foreign reflections may be identified and eliminated by the algorithms of image processing. As a result, ascertaining the astigmatism axis is simplified or even only made possible. This procedure would also be assisted by the individual light sources optionally emitting light of different wavelengths or being operated in a pulsed fashion.

In addition to the astigmatism axis, it is also possible, for example, to derive the curvature of the cornea. In general, it is possible to refer to geometric or topographic parameters.

Preferably, light for generating the light marking on the eye is incident at an angle α to the axis of a capturing camera.

By way of example, this is achieved by virtue of the projector for generating the light marking not being integrated in the microscope but instead being situated outside of the microscope housing or being fastened thereto. As a result, the axis of the integrated microscope camera and the direction of incidence of the light marking include a non-vanishing angle. This fact may be used to determine the eye alignment.

The projector or pattern generator should, for example, project a line or a pair of lines onto the eye. The angle at which the pattern is generated on the eye in relation to the camera axis preferably lies in the range of 5 degrees to 85 degrees, particularly preferably between 5 degrees and 50 degrees. What is important here is that this angle is greater than zero so that the position of e.g. the limbus plane and hence the viewing direction may be calculated, for example by way of triangulation algorithms. As a result, distance information may be extracted from the image coordinates of the projected pattern. This is a great advantage in relation to, for example, a coaxial generation and capture of the light marking, in which the projection direction of the pattern and the camera axis do not include an angle therebetween.

Thus, using the pattern, it is firstly possible to communicate to the medical practitioner the torsional orientation which the IOL should have and, secondly, it is also possible to determine the viewing direction of the patient eye. To this end, the projected pattern is more complex than a line, for example a line pair. A plane in space emerges from three or more points of intersection of the pattern with the limbus. By way of example, it is possible to ascertain the distance to the pupil center using only one line.

The apparatus according to the invention for determining the orientation of the eye during an eye operation comprises: an illumination device for generating a light pattern on the eye of a patient in the operation position; and a camera device to capture the light pattern generated on the eye during the eye operation; as well as a computer unit configured to ascertain at least one property of the eye, which is dependent on the current orientation of the eye, from the captured light pattern during the eye operation.

The advantages described above in relation to the method also apply, mutatis mutandis, to the features of the apparatus according to the invention.

By way of example, the ascertained property or the parameter is a geometric, differential geometric, topographic, keratographic or optical property of the eye which characterizes the current orientation of the eye.

Advantageously, provision is made of a device for fastening to an operating microscope or for swiveling-in the illumination device. The advantages described above in conjunction with the method according to the invention are facilitated thereby and by the following features.

Advantageously, provision is made of a control unit configured to control a second illumination device for generating a light marking on the eye on the basis of the currently ascertained geometric parameter during the eye operation. However, for example, the control unit may also actuate an ablation laser on the basis of the current geometric parameter ascertained during the eye operation. Here, only the information in respect of the static torsion is transferred to the treatment laser. Thereupon, the latter turns its shot list or changes the shot positions.

The property or parameter ascertained from the light pattern for example characterizes a specific position-dependent characteristic of the eye. In particular, this property is a specific geometric, differential geometric, topographic, keratographic or optical property.

Advantageously, the property or parameter ascertained from the light pattern characterizes the position of the astigmatism axis of the eye or a direction with a defined relationship thereto.

Preferably, the illumination device for generating the light pattern is configured in such a way that it generates diffuse or afocal light.

In particular, provision is made of a second illumination device for generating a light marking on the eye, said second illumination device indicating information, such as e.g. the current orientation of an eye parameter and/or a spatial marking required for the operation, on the eye during the eye operation.

Advantageously, the light marking indicates the intended orientation of an intraocular lens to be inserted into the eye and/or the intended position of an incision to be carried out on the eye.

In particular, the light marking may indicate the astigmatism axis of the eye or an axis with a defined relationship thereto on the eye.

Advantageously, the control unit, on the basis of the information obtained about the torsion carried out, corrects the orientation of the shot pattern of the ablation laser on the basis of the currently ascertained geometric parameters of the eye during the laser treatment.

In particular, the illumination device for generating the light marking is arranged in such a way that the incidence occurs at an angle α to the axis of a capturing camera.

Advantageously, the illumination device is configured in such a way that specific reflection shapes are generated on the eye.

In accordance with one aspect of the invention, an operating microscope for eye surgery is developed, said operating microscope comprising an apparatus according to the invention.

In accordance with a further aspect of the invention, a control unit for eye surgery systems is developed, said control unit being configured to carry out the method according to the invention.

In particular, the control unit comprises a computer unit which ascertains at least one property or parameter of the eye from a light pattern ascertained on the eye during the eye operation, said property or parameter characterizing the current orientation of the eye, the control unit being configured in such a way that it controls an optical display apparatus and/or an ablation laser.

Furthermore, a computer program for controlling an eye surgery system is developed, said computer program comprising program steps for carrying out the method according to the invention.

Below, the invention is described in an exemplary manner on the basis of the figures. In detail.

Figure 1:
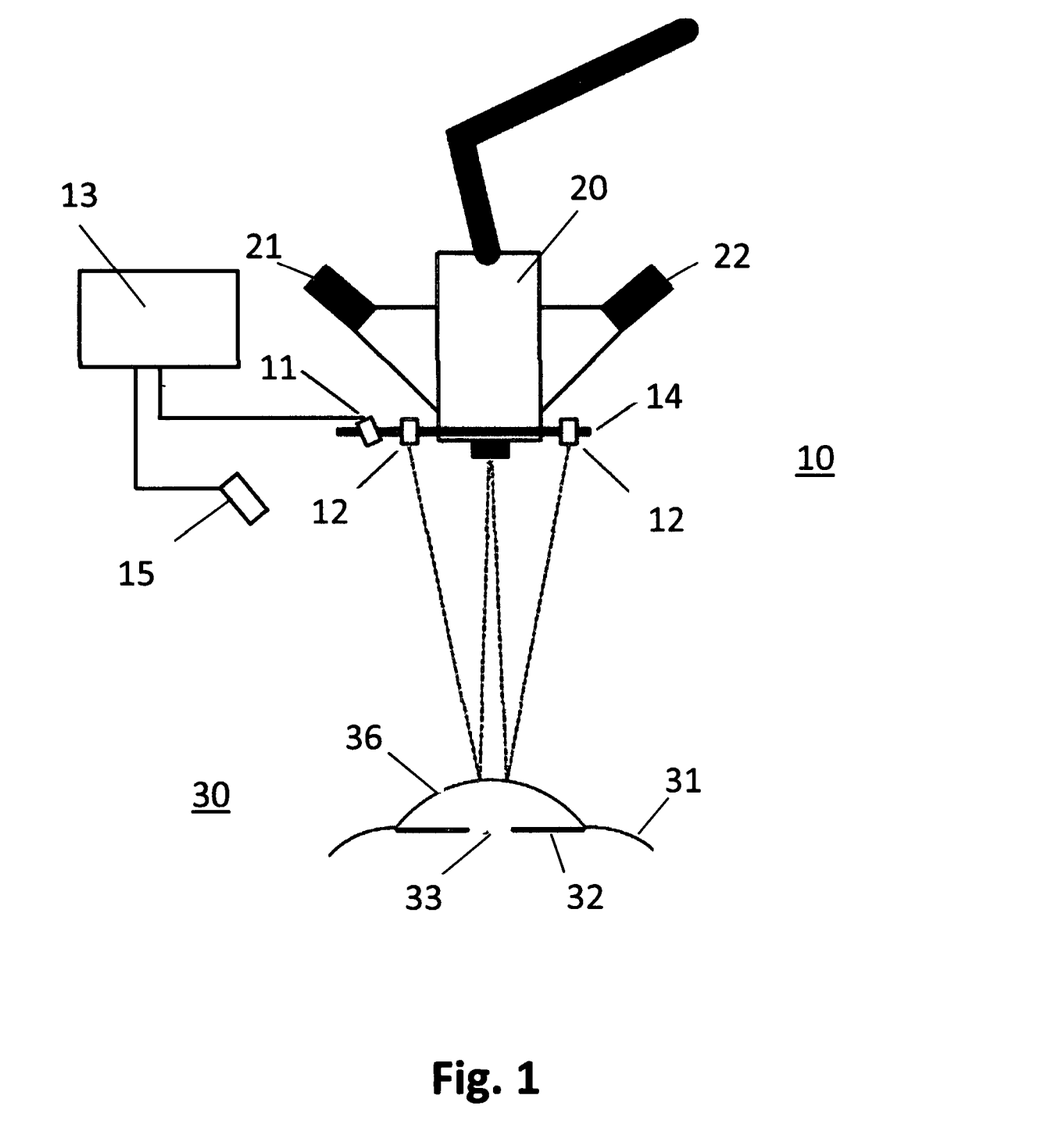
FIG. 1 shows an apparatus in accordance with a preferred embodiment of the invention, which is fastened to an operating microscope.

FIG. 1 shows an apparatus 10 in accordance with a preferred embodiment of the invention, which is fastened to an operating microscope 20. The operating microscope 20 comprises eyepieces 21, 22, through which the medical practitioner peers onto the eye 30 of the patient during the operation. The apparatus 10 for determining the orientation of the eye 30 is arranged on the side of the operating microscope 20 facing the eye 30. The apparatus 10 comprises a camera 11 and an illumination device 12 which serves to generate a light pattern on the eye 30. The camera 11 serves to capture the light pattern generated on the eye and is connected to a computer unit 13. From the captured light pattern, the computer unit 13 ascertains a parameter which is characteristic for the current orientation of the eye 30.

Appropriately designed light sources are used in order to generate diffuse light or afocal illumination by way of the illumination device 12. However, for example, diffusor elements may also be arranged in the beam path downstream of the light source as an attachment, for example if LEDs or optical waveguides serve as light sources of the illumination device.

A holder 14 which holds the camera 11 and the illumination device 12 and connects these to the operating microscope 20 serves as a fastening device. However, a camera integrated into the operating microscope may also serve to capture the light pattern generated on the eye.

The current orientation of the eye is understood to mean, in particular, the torsional position, i.e. the angle of rotation of the eye about the axis of the viewing direction.

Optionally, provision is additionally made of a second illumination device 15 or a light-pattern generator.

The second illumination device 15 serves to generate a light marking on the eye 30, the location or position of which light marking is controlled on the eye 30 on the basis of the parameter ascertained by the computer unit 13 from the image data of the camera 11. Advantageously, the second illumination device 15 is likewise fastened to the holder 14. It is also possible to determine the viewing direction with appropriate moving or static patterns.

The eye 30 comprises the sclera 31, the iris 32, the pupil 33 and the cornea 36.

Figure 2A:
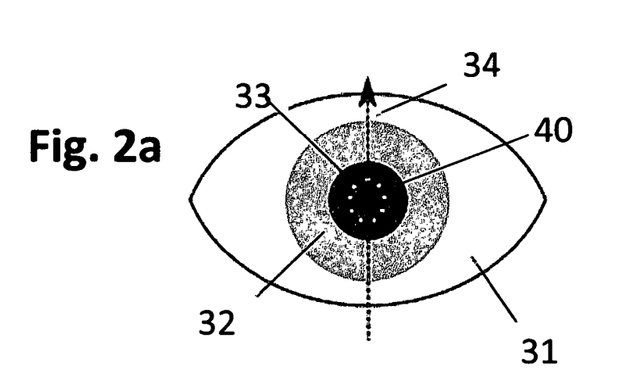
FIGS. 2a-2c show preferred examples of light patterns generated on the eye.
Figure 2B:
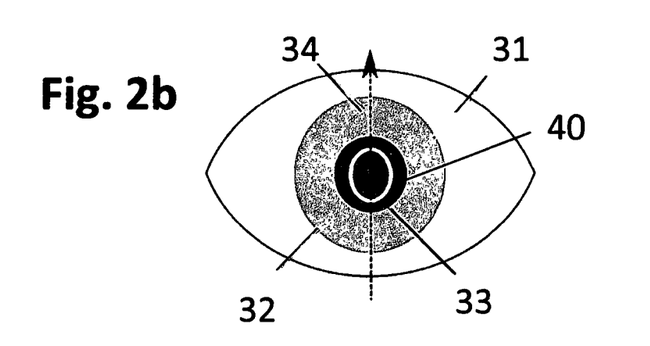
Figure 2C:
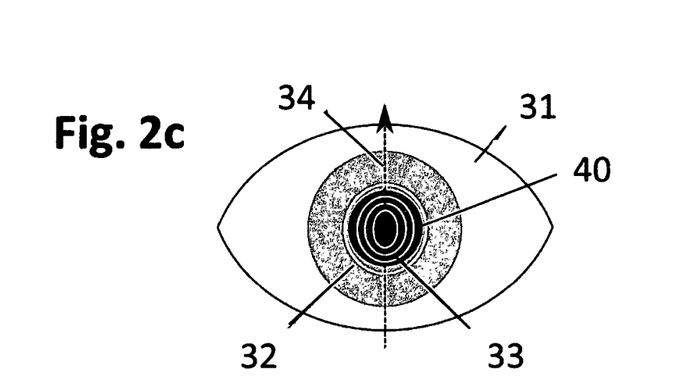

FIGS. 2a-2c show preferred examples of the light pattern 40 generated on the eye 30. Once again, the sclera 31, the iris 32 and the pupil 33 are shown as parts of the eye 30. The light patterns 40 arise as a result of the light reflections on the cornea of the eye 30.

The light pattern 40 shown in FIG. 2a consists of an ellipse-like arrangement of light points. In this example, the light points or the corneal light reflections are generated by a circular arrangement of LEDs with diffusor elements disposed upstream thereof as an illumination device 12 of the apparatus 10 (see FIG. 1). The deformation to an ellipse-like arrangement emerges from the astigmatism of the eye 30. The longitudinal axis of the ellipse approximately corresponds to the astigmatism axis 34 of the eye 30.

In FIG. 2*b*, a ring-shaped or circular diffuse light source is used as illumination device 12 (see FIG. 1) for illuminating the eye 30. An ellipse-like light reflection on the cornea of the eye 30 emerges as light pattern 40. In this example too, the ellipse-like form of the light pattern 40 arises from the astigmatism of the eye 30, with the semi-major axis of the ellipse approximately corresponding to the astigmatism axis 34 of the eye 30 and specifying the direction thereof.

An arrangement of a plurality of ring-shaped, diffuse light sources, which are arranged as concentric circles, is used in FIG. 2*c* as an illumination device for illuminating the eye 30. Ellipse-like light reflections on the cornea of the eye 30 emerge as light pattern 40. In this example too, the ellipse-like shape of the light pattern 40 arises from the astigmatism of the eye 30, the semi-major axes of the ellipses approximately corresponding to the astigmatism axis 34 of the eye 30 and specifying the direction thereof.

In accordance with the invention, it is not necessary for the torsion, i.e. the relative twist of the eye between diagnosis and operation, to be determined indirectly by means of image processing by an image-feature-based comparison between a diagnostic image and an operation image. Instead, relevant parameters of the eye, such as e.g. the astigmatism axis, are determined directly during the operation by e.g. topometric, topographic, keratometric, keratographic or ophthalmometric measurements. Hence, there is independence from the image material of the diagnosis.

Figure 3A:
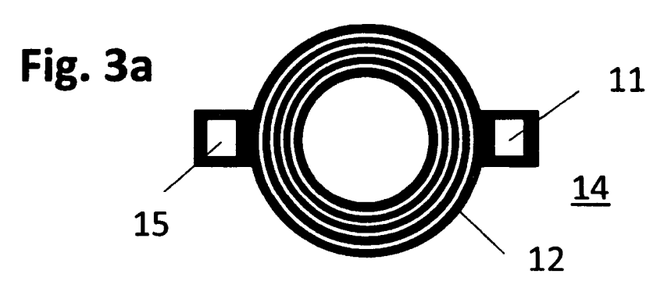
FIGS. 3a and 3b show different light-source arrangements as an illumination device for generating light patterns on the eye.
Figure 3B:
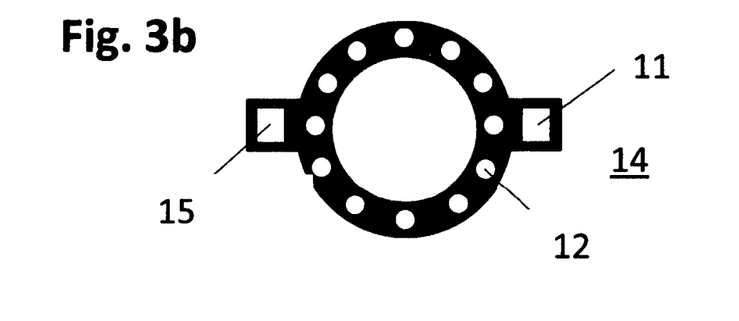

FIGS. 3*a* and 3*b* show, in a plan view from below, i.e. as seen from the operation object or the patient eye, a fastening device 14 with the camera 11, the illumination device 12 for generating the light pattern and the second illumination device 15. The illumination device 12 comprises a ring-shaped arrangement of diffuse or afocal light sources. The camera 11 is optional for the case where the integrated camera of the operating microscope is not used. Various light-source arrangements for generating the light pattern on the eye 30 are shown as illumination device 12.

The light sources of the illumination device 12 generate diffuse or afocal light. To this end, the holder 14 (see FIG. 1) may be equipped with a number of LEDs with diffusor elements placed in front thereof (FIG. 3*b*) or e.g. with diffusely luminous rings which are embodied as concentric circles (FIG. 3*a*). However, instead of the luminous LEDs or rings, the use of bright, non-luminous points or circles which are illuminated by a secondary light source is also possible.

Figure 3C:
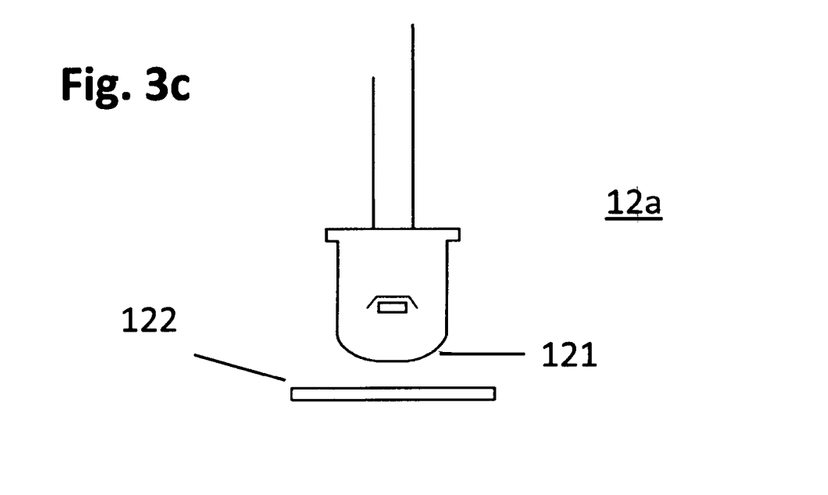
FIG. 3c shows a diffuse light source of the illumination device comprising a diffusor element.

FIG. 3*c* shows, as an example, a diffuse light source 12*a* of the illumination device 12 comprising an LED 121 and a diffusor element 122 arranged in front of the LED 121 as an attachment, said diffusor element being configured as a light-scattering film or glass pane.

Figure 3D:
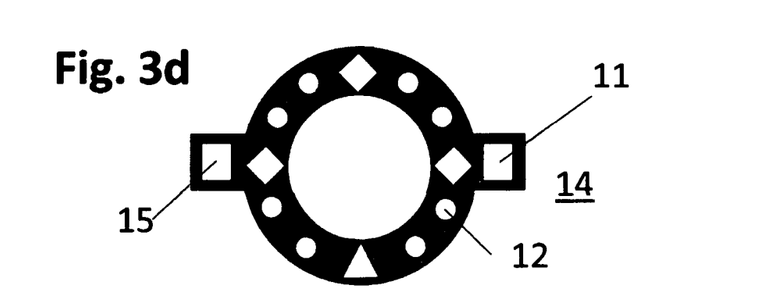
FIGS. 3d and 3e show illumination devices for generating specific reflection shapes on the eye.
Figure 3E:
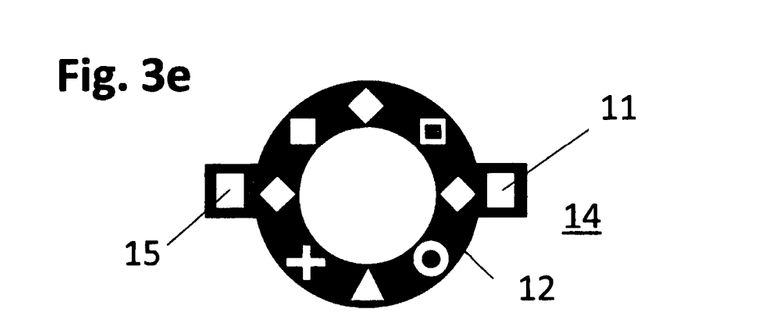

FIGS. 3*d* and 3*e* show, as further examples, the fastening device 14 as already described in FIGS. 3*a* and 3*b*, wherein the illumination device 12 is designed to generate specific reflection shapes on the eye. For this purpose, individual light elements or light sources 12*a* of the illumination device 12 have a specific geometric shape, which is designed in such a way that the light reflection generated through it on the eye differs from other light reflections or foreign reflections.

In the shown examples, the individual light sources of the illumination device 12 have a rectangular, square, rhomboid or else ring-shaped design, with the light sources being provided in a defined arrangement with their different geometric shapes. The light reflections generated thereby on the eye are very clearly visible and may be distinguished very easily from the light reflections on the eye originating from other light sources.

Optionally, or additionally, the individual light sources of the illumination device 12 may also be operated in a pulsed manner or may emit light with specific or different wavelengths in order to generate a specific reflection shape or a specific light reflection on the eye, which may be distinguished from other light reflections on the eye.

Figure 4A:
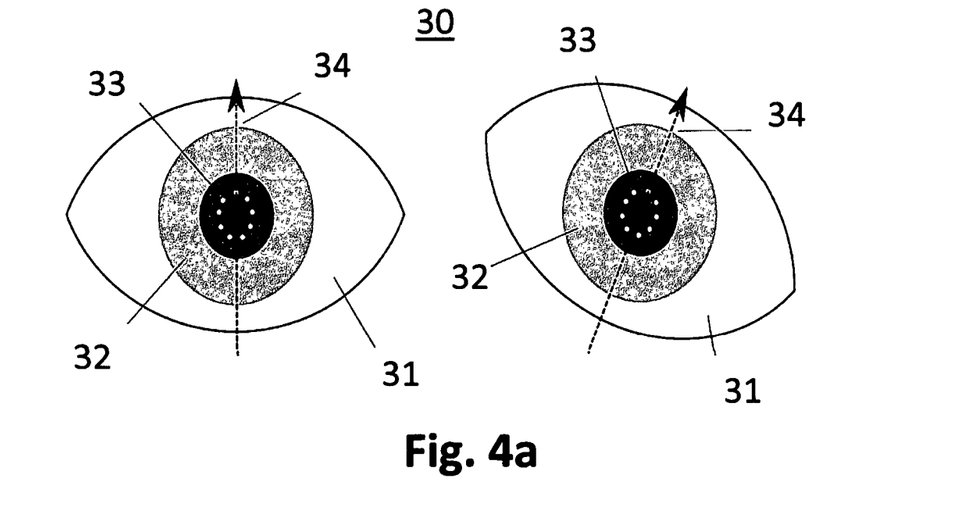
FIG. 4a shows images of the eye at the diagnosis and during the operation, wherein a twist or torsion of the eye about the viewing axis has taken place between the two recordings.

FIG. 4*a* shows, as an example, images of the eye 30 at the diagnosis (left image) and during the operation (right image), with a ring, as shown in FIG. 3*b* and described further above, equipped with LEDs and diffusor elements placed in front thereof being used as illumination device 12 (see FIG. 1). The reference signs in each case denote the same elements of the eye 30 as in the preceding figures. In this example, the position of the measured astigmatism axis 34 has changed at the time of the operation in relation to the position thereof at the time of the diagnosis. This change is referred to as static torsion. Errors due to this torsion are avoided by the invention.

Figure 4B:
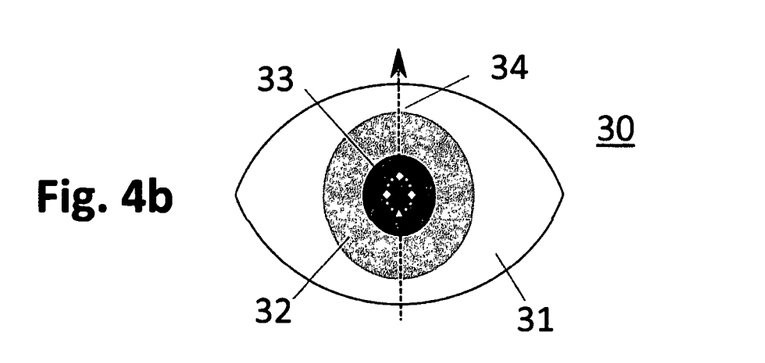
FIGS. 4b and 4c show images of the eye with light reflections having specific reflection shapes.
Figure 4C:
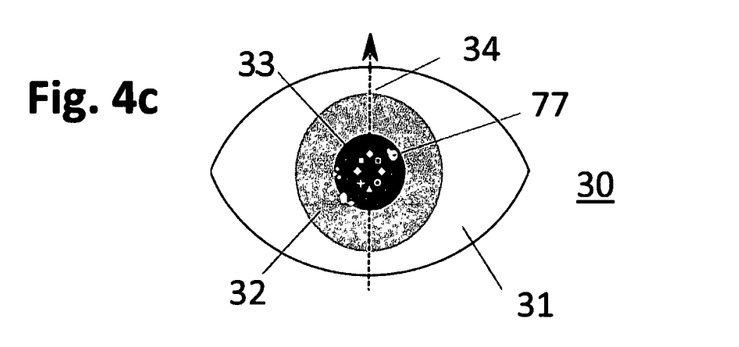

FIGS. 4*b* and 4*c* show, as further examples, images of the eye 30 with light reflections which have specific reflection shapes on the eye. The same reference signs as in the preceding figures denote the same elements and were already described above. The reflection shape depicted in FIG. 4*b* is generated by the illumination device 12 shown in FIG. 3*d*, while the reflection shape depicted in FIG. 4*c* is generated by the illumination device shown in FIG. 3*e*. For elucidation purposes, foreign reflections 77 are additionally shown in FIG. 4*c*; these are very easily identifiable as such on account of the specific reflection shape of the illumination device.

However, the ascertained position of the astigmatism axis 34 during the operation may, optionally, also be compared to the axis position during the diagnosis, said axis position preferably having been ascertained according to the same principle or else by means of a different method.

The measurement principle during the diagnosis and during the operation need not necessarily be identical. However, parameters which may be compared in terms of the spatial position thereof need to be derivable in each case. By way of example, a topographic measurement using so-called Placido rings may be carried out during the diagnosis, from which, initially, the spatially resolved surface curvature and, subsequently, both the eye surface itself and the astigmatism axis may be calculated. On the other hand, the eye surface may be measured as a point cloud during the operation, for example by way of strip-projection techniques. The astigmatism axis 34 may also be derived therefrom. As already mentioned above, it is now possible, either, to compare the 3D surface point clouds to one another by means of registration or else only the orientation of the astigmatism axis derivable therefrom in each case, in order to ascertain the torsion between diagnosis and operation.

However, it is also possible to directly measure the eye surface during the diagnosis and the operation. Here, in particular, it is also possible to apply triangulation methods, strip-projection techniques, stereo vision or similar methods. As a result, a 3D point cloud, which represents the eye surface, is generated. The point clouds arising during diagnosis and operation may be compared to one another. From this registration process, it is likewise possible, inter alia, to calculate the torsion.

However, from a technical point of view, it is easiest if the same measurement method is used during the operation as at the diagnosis. By way of example, if a ring-like arrangement of LEDs with diffusor elements placed in front thereof is used during the diagnosis for an astigmatism measurement, then such an arrangement may likewise be used during the operation. The astigmatism axes ascertained in each case may subsequently be compared. The torsion emerges from the angle included between these axes.

Figure 5:
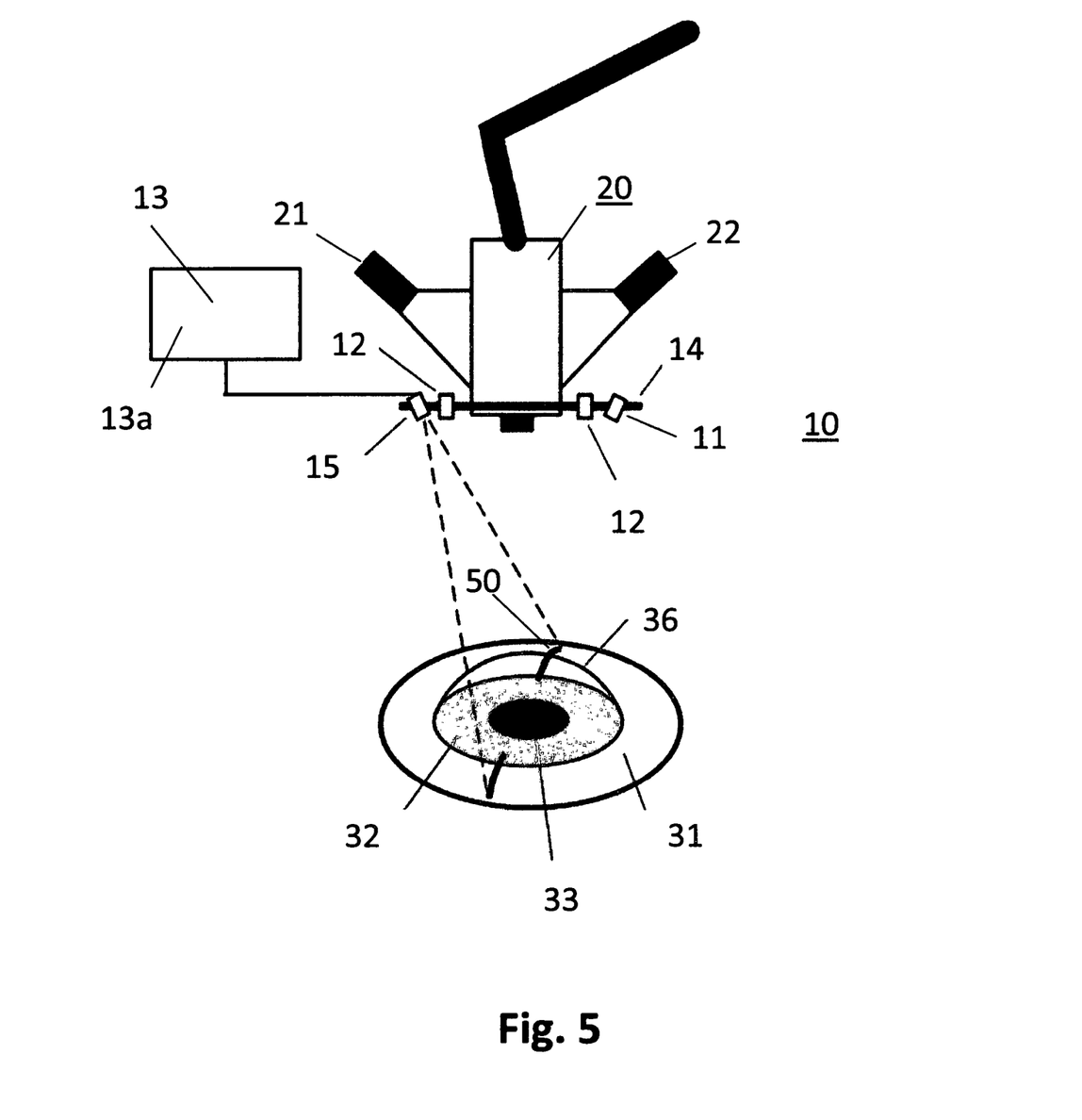
FIG. 5 shows an operating microscope comprising the apparatus according to the invention.

FIG. 5 shows an operating microscope 20 which comprises the apparatus 10 according to the invention. The elements of the operating microscope 20, including the apparatus 10 which is integrated therein or fastened thereto in a removable manner, are provided with the same reference signs as in FIG. 1. A light marking 50 is generated on the eye 30 by the second illumination device 15. The position and orientation of the light marking 50 on the eye 30 is controlled on the basis of the parameter ascertained by the computer unit 13 from image data of the camera 11 or an integrated microscope camera.

To this end, the computer unit serves as a control unit 13a or has the latter integrated therein. In this example, the astigmatism axis 34 of the eye 30 ascertained from the light pattern 40 during the operation (see FIGS. 2a to 2c) is indicated on the eye 30 by the light marking 50 and is therefore visible to the medical practitioner on the eye 30.

The elements of the eye 30 are as described above and provided with the same reference signs. The data connection between the camera 11 and the computer or control unit 13 or 13a is not depicted in FIG. 5 for reasons of clarity.

The position of the astigmatism axis 34 or the intended orientation of an intraocular lens to be inserted is projected directly onto the eye and therefore indicated to the medical practitioner directly on the eye by way of the second illumination device 15 in the form of a projector or a laser, such as e.g. a line or point laser.

To this end, the computer unit 13 evaluates the camera images of the microscope and instructs the projector or a pattern generator to generate e.g. a line as light marking 50 which, for example, indicates the astigmatism axis 34 of the eye 30 or an axis with a defined relationship thereto. Other information is also expedient, such as e.g. the locations at which incisions should be performed. The position thereof is also determined by evaluating the reflections of the light sources or the illumination device 12 generated on the cornea.

The computer unit 13 may additionally track the eye 30 so that the projector or laser is always able to generate the line at the same position, e.g. always at the center of the limbus. That is to say, the computer unit 13 is able to simultaneously track the eye, e.g. the pupil or the limbus, and instruct the projector or the second illumination device 15 to project the intended axis, which is visible to the medical practitioner, in the center of the pupil or the center of the limbus.

Tracking algorithms may ascertain the current eye position, including the torsion, and thus facilitate the projection of e.g. a co-migrating intended axis of the intraocular lens onto the eye. The display of further information is also possible, such as the locations at which the incisions should be made, the edge of the limbus, the optical and visual axes of the patient, the position of the capsulorhexis, etc.

If use is made of a projector or, in general, a pattern generator as an illumination device 15 which is provided for visualizing e.g. the astigmatism axis, it is also possible to generate 3D data with the aid of the camera 11 or the internal microscope camera, which includes an angle with the projection or illumination device 15, where necessary. A point cloud representing the eye surface or parts thereof is generated in the computer unit 13 with the aid of specific static or moving patterns. As a result thereof, it is possible, for example, to determine the viewing direction of the eye 30. If there is a certain amount of asphericity of the eye surface or of parts thereof, this also allows the dynamic or intraoperative torsion to be determined. It is likewise possible to ascertain the orientation of operating instruments situated in the field of view of the pattern and the camera 11.

When collecting the intraoperative eye data, for example with the aid of the reflections or with the aid of the aforementioned pattern generator, reflections also arise on the intraocular lens in the case of an appropriate angle of incidence, which reflections may be used for determining a position. Using this, it is possible, for example, to compare the axis of a toric lens with the astigmatism axis of the cornea and thus ascertain a possible incorrect orientation of the intraocular lens. It is likewise possible to detect an oblique position of the lens.

Figure 6:
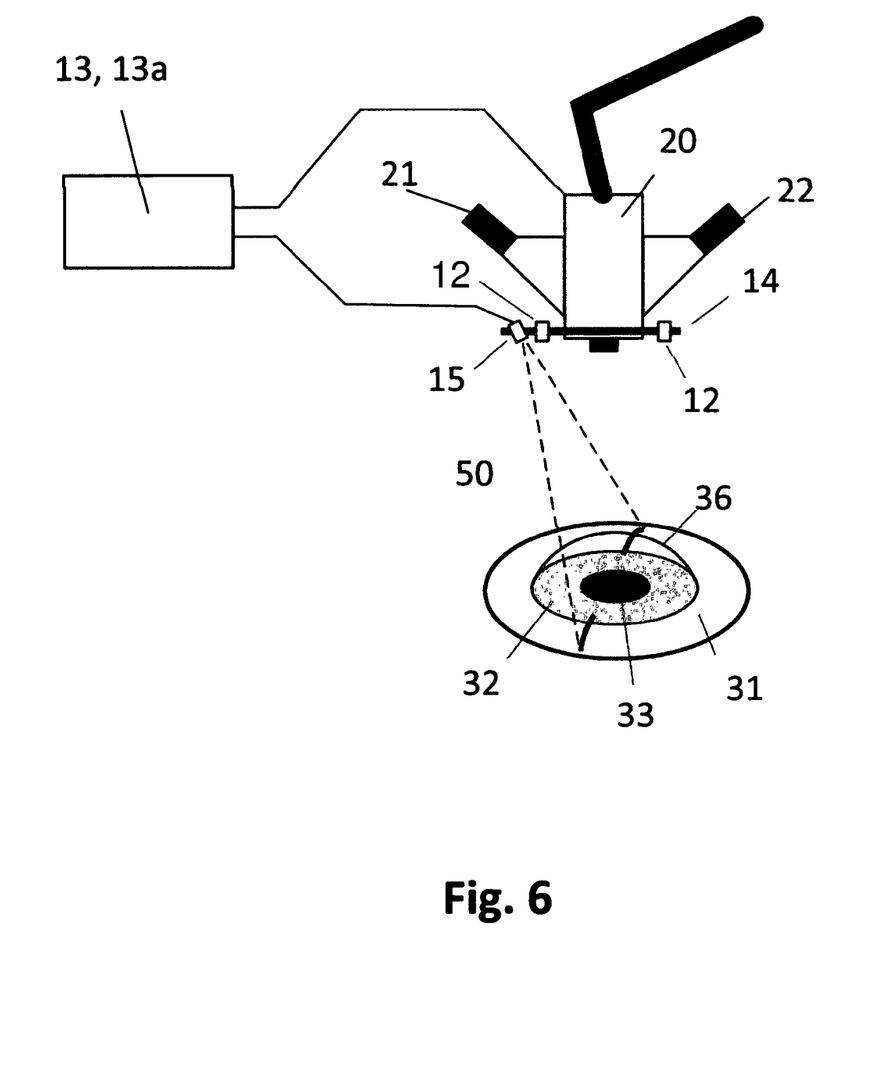
FIG. 6 shows an operating microscope according to the invention, in which the internal camera of the operating microscope is used as a camera for capturing the light pattern generated on the eye.

FIG. 6 shows an operating microscope 20 according to the invention, in which the internal camera of the operating microscope 20 is used as camera 11 for capturing the light pattern generated on the eye. The elements denoted by the further reference signs were already described above.

Figure 7:
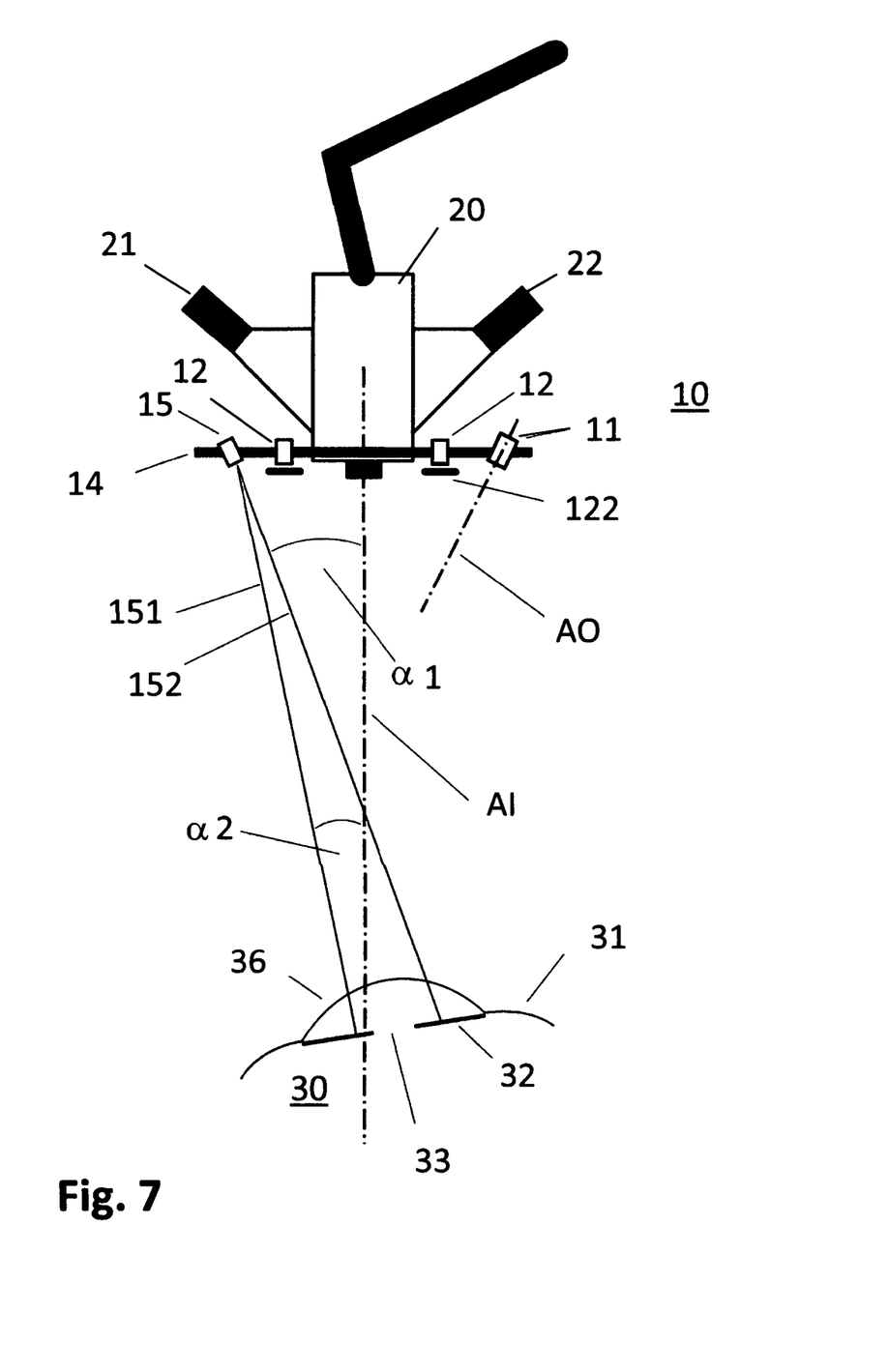
FIG. 7 shows an operating microscope which comprises the apparatus 10 according to the invention, with an illustration of the angles α1 and α2 with the optical axis of the internal camera for capturing the image of the eye.

FIG. 7 shows an operating microscope 20 which comprises the apparatus 10 according to the invention, as already described in relation to FIGS. 1 and 5. For reasons of clarity, the computer unit 13 (see FIG. 5) has not been depicted in this figure. The depicted elements are provided with the same reference signs as in FIGS. 1 and 5. Additionally, diffusor elements 122, which are placed in front of the LEDs of the first illumination device 12, are explicitly depicted. The camera 11 is optional for the case where the integrated camera of the operating microscope is not used for capturing the light patterns on the eye 30. However, it may also be used in addition to an integrated camera of the operating microscope.

In the example shown here, the second illumination device 15 in the form of a pattern generator generates a line pair 151, 152, which is projected onto the eye 30. The individual lines 151, 152 include the angles α1 and α2 with the optical axis AI of the internal camera of the operating microscope 20. These angles are advantageously of the order of approximately 5 to 45 degrees. The angles which the lines 151, 152 include with the optical axis of the optional camera 11 are not depicted for reasons of clarity.

The fact that the angles α1 and α2 are greater than zero facilitates the determination of alignment or tilt of the eye 30. The greater the tilt or rotation of the eye about the horizontal and vertical axes thereof, the less the center of the reflections coincides with the apex of the cornea 36. As a result, the statements from the calculations based on the reflection patterns no longer relate to the corneal apex. Depending on the tilt, the calculated astigmatism axis may deviate from the central astigmatism axis and it is therefore only still comparable with the astigmatism axis during the diagnosis to restricted extent.

Figure 8:
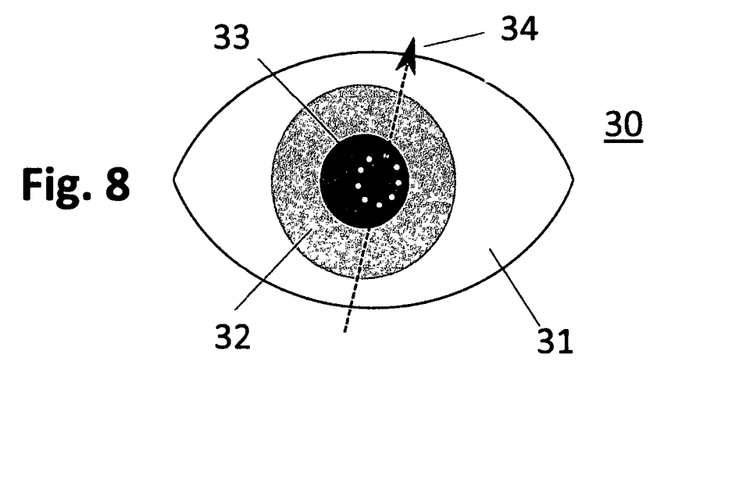
FIG. 8 shows an image of an eye which is tilted or rotated to the right in the illustration.

By way of example, an eye tilt of 5° already results in a decentration of 1 mm of the light reflection center from the apex. This value rises to approximately 2 mm at 10°. For elucidation purposes, the decentration is depicted in FIG. 8, wherein the eye 30 is rotated to the right in the shown example. The employed reference signs denote the elements of the eye 30 as already described above.

The fact that the center of the reflections and the center of the pupil or the limbus do not correspond in the camera image may only be used to restricted extent for determining a tilt since there need not necessarily be a coincidence between reflection center and center of pupil or limbus in the case of an asymmetrically shaped limbus or pupil, even in the case of a vanishing tilt. It is also possible that the limbus, in part, is so out of focus that the limbus center may no longer be reliably identified or determined.

By way of example, the tilt may be detected by virtue of generating a light pattern on the eye at arbitrary times with the aid of a pattern generator. This is shown as an example in FIG. 9. The employed reference signs denote the elements of the eye 30 as were already described above.

Figure 9:
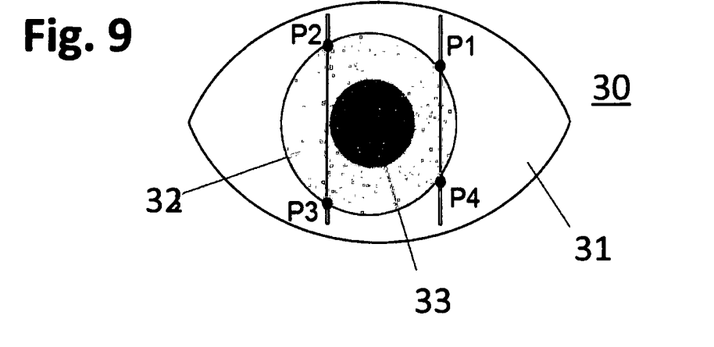
FIG. 9 shows an image of an eye with a light pattern projected thereon for detecting a tilt of the eye.

In order to determine the tilt of the eye 30, the points of intersection P1, P2, P3, P4 of the light pattern, which is a line pair in the depicted example and which is projected onto the eye 30 as shown in FIG. 7, with the limbus are ascertained. Subsequently, the 3D-coordinates of these points of intersection P1, P2, P3, P4 are calculated after a preceding, patient-independent calibration process, with the aid of which 3D-coordinates an equalization plane is approximated. Finally, the normal of the plane specifies the eye orientation. The shown line pair is only one example of many possible patterns. However, there must be at least three points not lying on one line.

It is also possible to combine displaying the astigmatism axis 34 and calculating the tilt, for example by virtue of generating a relatively tight line pair on the eye 30, which, on the one hand, ascertains a tilt and, on the other hand, displays the ascertained astigmatism axis. In particular, a specific color or blinking of the lines generated on the eye supplies the medical practitioner with indications for the current tilt.

Alternatively, the eye orientation may also be ascertained without a pattern generator but with the aid of an additional camera by means of stereo vision. To this end, the edge of the limbus, for example, is detected in both camera images in order subsequently to use the respective image coordinates for calculating the spatial position thereof.

A substantial advantage of the system and method according to the invention lies in the fact that the re-measurement of eye parameters, such as e.g. the astigmatism axis, means that there is no dependence on image material from the diagnosis.

In particular, it is possible to introduce intraocular lenses with a high accuracy at the envisaged position, for example in relation to the axis position of the eye, into the eye without a torsion of the eye during the operation, or between the time of diagnosis and the time of operation, impairing the accuracy. In the process, the lens axis may be oriented along the axis position of the eye, which is visible to the medical practitioner during the operation.

The static torsion, in particular, may be measured very well during laser treatments. It is also possible, for example, to rotate shot patterns during laser treatments in accordance with the measured intraoperative axis position prior to the start of the treatment such that the treatment errors as a result of the static torsion are avoided.

The invention claimed is:

1. A method of determining an orientation of an eye of a patient during an eye operation, the method comprising:
generating a light pattern on the eye;
capturing the light pattern while the patient is in an operation position; and
determining at least one property of the eye from the light pattern captured when the patient is in the operation position, said property characterizing the current orientation of the eye,
wherein the light pattern on the eye is generated by a diffuse or afocal illumination source,
wherein the diffuse or afocal illumination source has a light element and a diffuser element configured so that the light pattern generated on the eye is composed of diffuse light.

2. The method as claimed in claim 1, further comprising:
controlling, using the property determined from the light pattern, generation of a light marking on the eye during the eye operation.

3. The method as claimed in claim 1, wherein the property determined from the light pattern is a specific topographic property of the eye.

4. The method as claimed in claim 1, wherein the property determined from the light pattern comprises a position of the astigmatism axis of the eye and/or a direction with a defined relationship thereto.

5. The method as claimed in claim 1, wherein the property is determined from the light pattern by collecting data of the eye during the operation, the data being obtained from topometric, topographic, keratometric, keratographic or ophthalmometric measurements.

6. The method as claimed in claim 5, wherein the data, or variables derivable therefrom, are compared to corresponding data ascertained during a diagnosis, or variables derivable therefrom, in order to determine a change in position of the eye during the operation in relation to the time of the diagnosis.

7. The method as claimed in claim 5, wherein the data collected during the operation and associated images are stored and used as reference data or reference images for subsequent image-processing-based steps.

8. The method as claimed in claim 2, wherein the light marking indicates one or more of the following information items on the eye during the eye operation:
a spatial marking which is required or helpful for the operation;
an intended orientation of an intraocular lens to be inserted into the eye;
an intended position of an incision to be carried out;
a position of limbus and/or pupil;
a direction of the astigmatism axis or a direction with a defined relationship thereto.

9. The method as claimed in claim 2, wherein light for generating the light marking on the eye is incident at an angle α to an axis along which the light pattern on the eye is captured.

10. The method as claimed in claim 1, wherein the light pattern generated on the eye comprises specific reflection forms.

11. An apparatus for determining an orientation of an eye of a patient during an eye operation, the apparatus comprising:
an illumination device configured to generate a light pattern on the eye of the patient in an operation position;
a camera device configured to capture the light pattern generated on the eye during the eye operation; and
a computer configured to ascertain at least one property of the eye, which is dependent on the current orientation of the eye, from the captured light pattern during the eye operation,
wherein the illumination device is configured to generate diffuse or afocal light for generating the light pattern,
wherein the illumination source has a light element and a diffuser element configured so that the light pattern generated on the eye is composed of diffuse light.

12. The apparatus as claimed in claim 11, further comprising:
a fastening device configured to fasten the illumination device and/or the camera device to an operation microscope.

13. The apparatus as claimed in claim 11, further comprising:
a second illumination device; and
a control unit configured to control the second illumination device to generate a light marking on the eye on the basis of the currently ascertained property of the eye during the eye operation.

14. The apparatus as claimed in claim 11, wherein the property ascertained from the light pattern comprises a specific position-dependent characteristic of the eye and/or a specific topographic property of the eye and/or the position of the astigmatism axis or a direction with a defined relationship thereto.

15. The apparatus as claimed in claim 11, further comprising:
a second illumination device configured to generate, based on the property of the eye ascertained during the eye operation, a light marking on the eye, which displays one or more of the following information items on the eye during the eye operation:
a spatial marking which is required or helpful for the operation;
an intended orientation of an intraocular lens to be inserted into the eye;
an intended position of an incision to be carried out;
a position of limbus and/or pupil;
the direction of the astigmatism axis or a direction with a defined relationship thereto.

16. The apparatus as claimed in claim 11, further comprising:
a second illumination device configured to generate, based on the property of the eye ascertained during the eye operation, a light marking on the eye in such a way that light for generating the light marking is incident at an angle α to an axis along which the light pattern on the eye is captured.

17. The apparatus as claimed in claim 11, wherein the illumination device is configured to generate the light pattern comprising specific reflection forms on the eye.

18. An operating microscope for eye operations, comprising an apparatus as claimed in claim 11.

19. A control unit for eye surgery systems, wherein the control unit is configured to carry out the method as claimed in claim 1.

20. A non-transitory storage medium that stores a computer program for causing a control unit controlling an eye surgery system, to execute the method as claimed in claim 1.

21. The method as claimed in claim 1, further comprising:
using the property determined from the light pattern to correct a position of ablation locations during a laser treatment of the eye, depending on the current orientation of the eye, and/or to determine a viewing direction.

22. The apparatus as claimed in claim 11, further comprising:
an ablation laser; and
a control unit configured to control the ablation laser on the basis of the currently ascertained property of the eye during the eye operation.

23. The apparatus as claimed in claim 11, wherein the illumination device comprises a plurality of light sources which have different geometric shapes, and/or are configured to generate light in a pulsed manner, and/or are configured to generate light at different wavelengths, to distinguish the generated light pattern from other light reflections on the eye.

24. A method of determining an orientation of an eye of a patient during an eye operation, the method comprising:
generating a light pattern on the eye of the patient by a diffuse or afocal illumination source which generates reflections on the eye, the afocal illumination source having a light element and a diffuser element configured so that the light pattern generated on the eye is composed of diffuse light;
capturing the light pattern generated and reflected on the eye; and
determining from the reflected and captured light pattern on the eye at least one property of the eye characterizing a torsional position of the eye,
wherein the reflected light pattern is captured and the torsional position of the eye is determined during the eye operation when the patient is in the operation position, and
controlling, using the torsional position determined from the light pattern, generation of a light marking on the eye during the eye operation by a second illumination source indicating a medical practitioner the current torsional position of the eye and/or a location marking required for the operation.

* * * * *